(12) United States Patent
Hamprecht et al.

(10) Patent No.: US 8,003,638 B2
(45) Date of Patent: Aug. 23, 2011

(54) 7-PYRAZOLYLBENZAZEPINES HAVING AFFINITY FOR D3 RECEPTOR

(75) Inventors: Dieter Hamprecht, Verona (IT); Fabrizio Micheli, Verona (IT); Luca Tarsi, Verona (IT); Giovanna Tedesco, Verona (IT)

(73) Assignee: Glaxo Group Limited, Middlesex (GB)

( * ) Notice: Subject to any disclaimer, the term of this patent is extended or adjusted under 35 U.S.C. 154(b) by 666 days.

(21) Appl. No.: 11/570,623

(22) PCT Filed: Jun. 17, 2005

(86) PCT No.: PCT/EP2005/006639
§ 371 (c)(1),
(2), (4) Date: Aug. 20, 2008

(87) PCT Pub. No.: WO2005/123717
PCT Pub. Date: Dec. 29, 2005

(65) Prior Publication Data
US 2008/0312213 A1 Dec. 18, 2008

(30) Foreign Application Priority Data
Jun. 21, 2004 (GB) .................................. 0413879.8

(51) Int. Cl.
A61P 25/00 (2006.01)
A61K 31/55 (2006.01)
C07D 401/14 (2006.01)
C07D 403/14 (2006.01)
C07D 413/14 (2006.01)
(52) U.S. Cl. .................................. 514/217.01; 540/594
(58) Field of Classification Search ............. 514/217.01; 540/594
See application file for complete search history.

(56) References Cited

FOREIGN PATENT DOCUMENTS

| WO | WO00/42036 | 7/2000 |
|---|---|---|
| WO | WO02/40471 A | 5/2002 |

OTHER PUBLICATIONS

Austin, et al., "Novel 2, 3, 4, 5-Tetrahydro-1H-3-benzazepines with High Affinity and Selectivity for the Dopamine D3 Receptor" *Bioorg. Med. Chem. Letters* (Nov. 20, 2000) 10(22)2553-2555 (XP004224262).
Ficker et al., *Circulation Research*, 82(3):386-395 (1998).
Ficker et al., *Molecular Pharmacology*, 60(6):1343-1348 (2001).
Kongsamut et al., *European Journal of Pharmacology*, 450:37-41 (2002).
Levant, *Pharmacological Reviews*, 49:231-252 (1997).
McConnell et al., *Science*, 257:1906-1912 (1992).
Schwartz et al., *Brain Research Reviews*, 26:236-242 (1998).
Smith et al., *Analytical Biochemistry*, 150:76-85 (1985).
Sokoloff et al., *Nature*, 347:146-151 (1990).
Tilford et al., *British Journal of Pharmacology*, 115:160 (1995).

*Primary Examiner* — Brenda Coleman
(74) *Attorney, Agent, or Firm* — Nora L. Stein; Theodore R. Furman

(57) ABSTRACT

Compounds of formula (I) or a salt thereof are disclosed:

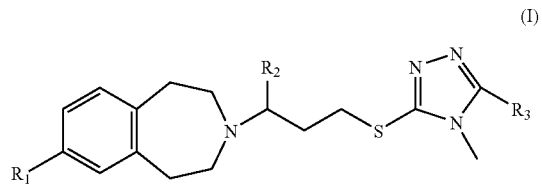

(I)

wherein $R_1$ is pyrazolyl substituted by two or three substituents independently selected from halogen, $C_{1-4}$alkyl and halo$C_{1-4}$alkyl; $R_2$ is hydrogen or methyl; and $R_3$ is quinolinyl, oxazolyl or phenyl, each of which is optionally substituted by one or two halogen, $C_{1-4}$alkyl or halo$C_{1-4}$alkyl. Processes for preparation and uses of the compounds in medicine, for example for the treatment of schizophrenia or drug dependency, are also disclosed.

6 Claims, No Drawings

7-PYRAZOLYLBENZAZEPINES HAVING AFFINITY FOR D3 RECEPTOR

This application is a §371 national phase entry of International Application No. PCT/EP2005/006639 filed 17 Jun. 2005.

The present invention relates to novel compounds, processes for their preparation, intermediates used in these processes, pharmaceutical compositions containing them and their use in therapy, as modulators of dopamine $D_3$ receptors, in particular as antipsychotic agents or as agents to treat various aspects of drug dependency.

WO2002/40471 (SmithKline Beecham) discloses certain benzodiazepine compounds having activity at the dopamine $D_3$ receptor. A novel class of compounds has now been discovered which fall within the generic scope of WO2002/40471 but are not specifically disclosed therein, and have been found to exhibit a surprisingly improved drug profile. These compounds are useful in the treatment of conditions wherein modulation, especially antagonism/inhibition, of the $D_3$ receptor is beneficial, e.g. as antipsychotic agents or to treat drug dependency.

The present invention provides a compound of formula (I) or a salt thereof:

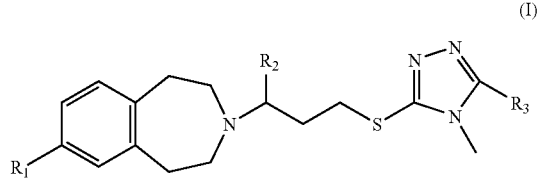

wherein:
 $R_1$ is pyrazolyl substituted by two or three substituents independently selected from halogen, $C_{1-4}$alkyl and halo$C_{1-4}$alkyl;
 $R_2$ is hydrogen or methyl; and
 $R_3$ is quinolinyl, oxazolyl or phenyl, each of which is optionally substituted by one or two halogen, $C_{1-4}$alkyl or halo$C_{1-4}$alkyl.

In formula (I), "—S—" means thio (sulfur).

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl.

The term "halogen" and its abbreviation "halo" refer to fluorine (F), chlorine (Cl), bromine (Br) or iodine (I).

The term "halo$C_{1-4}$alkyl" refers to $C_{1-4}$alkyl groups substituted by one or more halogen atoms, for example trifluoromethyl, trifluoroethyl, bromoethyl and trifluoropropyl.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, $R_1$ is pyrazol-5-yl or pyrazol-3-yl.
In one embodiment, $R_1$ is:
(a) a group of formula (i):

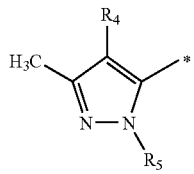

wherein $R_4$ is hydrogen or halogen (such as chloro) and $R_5$ is $C_{1-4}$alkyl (such as methyl) or halo$C_{1-4}$alkyl (such as $CH_2CF_3$); or
(b) a group of formula (ii):

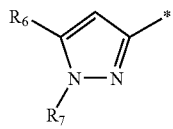

wherein $R_6$ and $R_7$ are independently $C_{1-6}$alkyl (such as methyl).

In one embodiment, $R_3$ is quinolinyl (such as quinolin-8-yl), substituted by one or two $C_{1-6}$alkyl (such as methyl) and/or one or two halogen (such as fluorine). For example, $R_3$ is 2-methyl-quinolin-8-yl. In another embodiment, $R_3$ is phenyl substituted by one or two $CF_3$ or halogen (such as fluorine). In another embodiment, $R_3$ is oxazolyl substituted by one or two $C_{1-6}$alkyl (such as methyl).

Examples of compounds of the present invention include:
1. 7-(1,3-dimethyl-1H-pyrazol-5-yl)-3-(3-{[4-methyl-5-(2-methyl-5-quinolinyl)-4H-1,2,4-triazol-3-yl]thio}propyl)-2,3,4,5-tetrahydro-1H-3-benzazepine;
2. 7-(1,3-Dimethyl-1H-pyrazol-5-yl)-3-(1-methyl-3-{[4-methyl-5-(2-methyl-5-quinolinyl)-4H-1,2,4-triazol-3-yl]thio}propyl)-2,3,4,5-tetrahydro-1H-3-benzazepine;
3. 7-(1,3-dimethyl-1H-pyrazol-5-yl)-3-[3-({4-methyl-5-[4-(trifluoromethyl)phenyl]-4H-1,2,4-triazol-3-yl}thio)propyl]-2,3,4,5-tetrahydro-1H-3-benzazepine
4. 3-(3-{[5-(3,4-difluorophenyl)-4-methyl-4H-1,2,4-triazol-3-yl]thio}propyl)-7-(1,3-dimethyl-1H-pyrazol-5-yl)-2,3,4,5-tetrahydro-1H-3-benzazepine
5. 7-(1,3-dimethyl-1H-pyrazol-5-yl)-3-(3-{[4-methyl-5-(4-methyl-1,3-oxazol-5-yl)-4H-1,2,4-triazol-3-yl]thio}propyl)-2,3,4,5-tetrahydro-1H-3-benzazepine 6. 7-(4-chloro-1,3-dimethyl-1H-pyrazol-5-yl)-3-(3-{[4-methyl-5-(4-methyl-1,3-oxazol-5-yl)-4H-1,2,4-triazol-3-yl]thio}propyl)-2,3,4,5-tetrahydro-1H-3-benzazepine
7. 7-(1,3-dimethyl-1H-pyrazol-5-yl)-3-(3-{[5-(8-fluoro-2-methyl-5-quinolinyl)-4-methyl-4H-1,2,4-triazol-3-yl]thio}propyl)-2,3,4,5-tetrahydro-1H-3-benzazepine
8. 7-(1,3-dimethyl-1H-pyrazol-5-yl)-3-(3-{[4-methyl-5-(2-methyl-6-quinolinyl)-4H-1,2,4-triazol-3-yl]thio}propyl)-2,3,4,5-tetrahydro-1H-3-benzazepine and salts thereof.

It will be appreciated that for use in medicine the salts of the compounds of the invention should be pharmaceutically (i.e physiologically) acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other non-pharmaceutically acceptable salts e.g. oxalates, may be used, for example in the isolation of compounds of the invention and are included within the scope of this invention. Also included within the scope of the invention are solvates, hydrates, complexes and prodrugs of compounds of the invention.

Certain of the compounds of the invention may form acid addition salts with one or more equivalents of the acid. The present invention includes within its scope all possible stoichiometric and non-stoichiometric forms. Certain of the compounds of the invention may form acid addition salts with less than one equivalent of the acid, or one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic rings included in compounds of formula (I) may exist in one or more tautomeric forms. The present invention includes within its scope all such tautomeric forms, including mixtures. For example, where $R_2$ is methyl, the present invention includes both of the following isomeric forms:

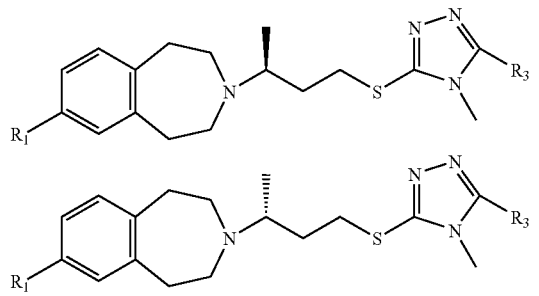

In one embodiment of the present invention compounds are provided e a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertible in the mammalian (e.g. human) body to the inventive compounds are however included.

The compounds of the present invention may be prepared using the methods disclosed in, for example, WO2002/40471. Thus the present invention also provides a process for preparing a compound of formula (I), which process comprises:

(a) reacting a compound of formula (II):

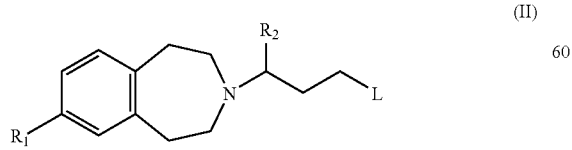

(II)

wherein $R_1$ and $R_2$ are as defined for formula (I) and L is a leaving group; with a compound of formula (III):

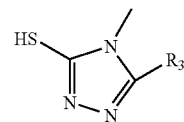

(III)

wherein $R_3$ is as defined for formula (I); or (b) reacting a compound of formula (IV):

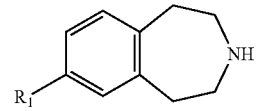

(IV)

wherein $R_1$ is as defined for formula (I), with a compound of formula (V):

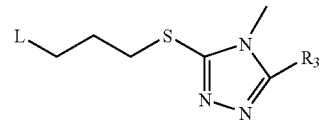

(V)

wherein $R_3$ is as defined for formula (I), and L is a leaving group; or (c) reacting a compound of formula (VI):

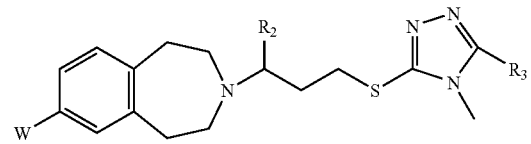

(VI)

wherein $R_2$ and $R_3$ are as defined for formula (I) and W is halogen or a perfluoroalkylsulfonyloxy group, or W is a group M selected from a boron derivative (e.g. a boronic acid function $B(OH)_2$) or a metal function such as trialkylstannyl (e.g. $SnBu_3$), zinc halide or magnesium halide; with a compound of formula (VII):

Pyr-$W_1$ (VII)

wherein Pyr is pyrazolyl substituted by two or three substituents independently selected from halogen, $C_{1-4}$alkyl and halo$C_{1-4}$alkyl, and $W_1$ is halogen or a perfluoroalkylsulfonyloxy group when W is a group M, or $W_1$ is a group M as defined above when W is halogen or a perfluoroalkylsulfonyloxy group;

and optionally thereafter for any of the steps (a), (b) or (c):
  removing any protecting group(s); and/or
  forming a salt; and/or
  converting one compound of formula (I) to a different compound of formula (I).

Process (a) may be effected using conventional methods for the formation of a thioether. The leaving group L can be halogen such as chlorine. Alternatively L can be a sulfonyloxy group such $C_{1-4}$alkylsulfonyloxy (e.g. methanesulfonyloxy or trifluoromethanesulfonyloxy); or AR'-sulfonyloxy wherein AR' is optionally substituted phenyl, an optionally substituted 5- or 6-membered aromatic heterocyclic group, or an optionally substituted bicyclic group, preferably optionally substituted phenyl, wherein in each case the optional substituents are one or more $C_{1-2}$alkyl groups; e.g. para-toluenesulfonyloxy. When L is a halogen the reaction may be carried out using a base such as lithium hydroxide in a solvent such as N,N-dimethylformamide.

In step (b), the leaving group, L, in compounds of formula (V) may be for example halogen, such as chlorine. The process of the present invention may be effected using conventional conditions for N-alkylation. For example, when L is a halogen such as chlorine, the reaction may be carried out in the presence of a source of iodide such as sodium iodide using a base such as potassium carbonate in a suitable solvent such as DMF at an appropriate temperature such as around 60° C. Alternatively L may be for example a sulfonyloxy group such as $C_{1-4}$alkylsulfonyloxy (e.g. methanesulfonyloxy or trifluoromethanesulfonyloxy); or arylsulfonyloxy wherein aryl is optionally substituted phenyl, e.g. para-toluenesulfonyloxy.

The reaction in process (c) may be effected in the presence of a transition metal e.g., palladium catalyst such as bis-triphenylphosphinepalladium dichloride or tetrakis-triphenylphosphinepalladium (0). When M is a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably halogen such as bromine, or a sulfonyloxy group such as trifluoromethylsulfonyloxy; and $W^1$ is preferably a group M, such as trialkylstannyl or B$(OH)_2$.

Compounds of formula (I) have been found to exhibit affinity for dopamine receptors, in particular the $D_3$ receptor, and are expected to be useful in the treatment of disease states which require modulation of such receptors, such as drug dependency or psychotic conditions. Many of the compounds of formula (I) have also been found to have greater affinity for dopamine $D_3$ than for $D_2$ receptors.

The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the more recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). Preferred compounds of the present invention are therefore those which have higher (e.g. >10× or >100× higher) affinity for dopamine $D_3$ than dopamine $D_2$ receptors (such affinity can be measured using standard methodology for example using cloned dopamine receptors—see herein). Said compounds may advantageously be used as selective modulators of $D_3$ receptors.

The compounds of the present invention have an unexpectedly advantageous drug profile. For example, some of the example compounds below have been shown to have low affinity for the human "ether-a-go-go" (hERG) potassium channel. hERG channel inhibition is used as an indication of the ability of a drug to affect QT interval (see for example Kongsamut et al, *European Journal of Pharmacology* 450 (2002), 37-41).

Compounds of formula (I) will be used for treatment of all aspects of drug dependency including prevention of relapse to and relief of withdrawal symptoms from drugs of abuse such as nicotine, alcohol, cocaine, amphetamine, metamphetamine, opiates, benzodiazepines, inhalants and inhibition of tolerance induced by opioids. In addition, compounds of formula (I) and pharmaceutically acceptable salts and solvates thereof will be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the maintenance of drug dependence and the probability of relapse or reinstatement of drug seeking and drug taking behaviors. The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). From the localisation of D3 receptors, it could also be envisaged that the compounds could also have utility for the treatment of substance abuse where it has been suggested that D3 receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

In a further aspect therefore the present invention provides a method of treating a condition for which modulation (especially antagonism/inhibition) of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. Such conditions in particular include psychoses/psychotic conditions such as schizophrenia, and substance abuse and/or drug dependency. For example, the condition to be treated may be craving for abused substance and/or relapse to drug seeking and drug taking behaviour.

The invention also provides the use of a compound of formula (I) or a pharmaceutically acceptable salt thereof in the manufacture of a medicament for the treatment of a condition in a mammal for which modulation (especially antagonism/inhibition) of dopamine receptors (especially dopamine $D_3$ receptors) is beneficial.

The invention also provides a compound of formula (I) or a pharmaceutically acceptable salt thereof for use in the treatment of a condition in a mammal for which modulation (especially antagonism/inhibition) of dopamine receptors (especially dopamine $D_3$ receptors) is beneficial.

In one embodiment, $D_3$ antagonists according to the present invention are used in the treatment of psychoses such as schizophrenia or in the treatment of substance abuse and/or drug dependency.

Thus, a still further aspect the invention provides a method of treating a psychotic condition (e.g. schizophrenia) or substance abuse and/or drug dependency which comprises administering to a mammal (e.g. human) in need thereof an effective amount of a compound of formula (I) as herein defined or a pharmaceutically acceptable salt thereof.

Also provided is the use of a compound of formula (I) or a pharmaceutically acceptable salt thereof in the manufacture of a medicament for the treatment of a psychotic condition (e.g. schizophrenia) or substance abuse and/or drug dependency in a mammal.

Also provided is a compound of formula (I) or a pharmaceutically acceptable salt thereof for use in the treatment of a psychotic condition (e.g. schizophrenia) or substance abuse and/or drug dependency in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Binding Experiments on Cloned Dopamine (e.g. D2, D3 and D4) Receptors

The ability of the compounds to bind selectively to human D2/D3/D4 dopamine receptors can be demonstrated by measuring their binding to cloned receptors. The inhibition constants ($K_i$) of test compounds for displacement of [$^{125}$I]-Iodosulpride binding to human D2/D3 and [$^3$H]-YM-09151 to D4 dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −80° C. Crude cell membranes were prepared by homogenisation followed by high-speed centrifugation, and characterisation of cloned receptors achieved by radioligand binding.

Preparation of Cho Cell Membranes: Cell Pellets were Gently Thawed at Room temperature, and resuspended in about 20 volumes of ice-cold Extraction buffer; 5 mM EDTA, 50 mM Trizma pre-set crystals (pH7.4@37° C.), 1 mM $MgCl_2$, 5 mM KCl and 120 mM NaCl. The suspension was homogenised using an Ultra-Turrax at full speed for 15 seconds. The homogenate was centrifuged at 18,000 r.p.m for 15 min at 4° C. in a Sorvall RC5C centrifuge. Supernatant was discarded, and homogenate re-suspended in extraction buffer then centrifugation was repeated. The final pellet was resuspended in 50 mM Trizma pre-set crystals (pH 7.4 @ 37° C.) and stored in 1 ml aliquot tubes at −80° C. (D2=3.0E+08 cells, D3=7.0E+07 cells and D4=1.0E+08 cells). The protein content was determined using a BCA protocol and bovine serum albumin as a standard (Smith, P. K., et al., Measurement of protein using bicinchoninic acid. Anal. Biochem. 150, 76-85 (1985)).

Binding experiments: Crude D2/D3 cell membranes were incubated with 0.03 nM [125I]-Iodosulpride (~2000 Ci/mmol; Amersham, U. K.) and D4 with 0.8 nM [$^3$H]-YM-09151 (~85 Ci/mmol; NEN, UK), and the test compound in a buffer containing 50 mM Trizma pre-set crystals (pH 7.4 @ 37° C.), 120 mM NaCl, 5 mM KCl, 2 mM $CaCl_2$, 1 mM $MgCl_2$, 0.3% (w/v) bovine serum albumin. The total volume is 0.2 ml and incubated in a water bath at 37° C. for 40 minutes. Following incubation, samples were filtered onto GF/B Unifilters using a Canberra Packard Filtermate, and washed four times with ice-cold 50 mM Trizma pre-set crystals (pH 7.4 @ 37° C.). The radioactivity on the filters was measured using a Canberra Packard Topcount Scintillation counter. Non-specific binding was defined with 10 µM SKF-102161 (YM-09151). For competition curves, 10 serial log concentrations of competing cold drug were used (Dilution range: 10 µM-10 pM). Competition curves were analysed using Inflexion, an iterative curve fitting programme in Excel. Results were expressed as pKi values where pKi=−log 10[Ki].

The exemplified compounds have pKi values within the range of 7.5-9.5 at the dopamine D3 receptor. pKi results are only estimated to be accurate to about ±0.3-0.5.

Functional Activity at Cloned Dopamine Receptors

The functional activity of compounds at human D2 and human D3 receptors (i.e. agonism or antagonism) may be determined using a Cytosensor Microphysiometer (McConnell H M et al Science 1992 257 1906-1912). In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16-18h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90s. The pump was on for the first 60s and the acidification rate determined between 68 and 88s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. & Baxter, G. S. Br. J. Pharmacol. (1995), Vol. 115, 160P]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

hERG Assay

Affinity at hERG may be measured by methods known to the skilled person, for example as described in Ficker, Eckhard; Jarolimek, Wolfgang; Kiehn, Johann; Baumann, Arnd; Brown, Arthur M. "Molecular determinants of dofetilide block of HERG K+ channels." *Circulation Research* (1998), 82(3), 386-395; and Ficker, Eckhard; Jarolimek, Wolfgang; Brown, Arthur M. "Molecular determinants of inactivation and dofetilide block in ether a-go-go (EAG) channels and EAG-related K+ channels." *Molecular Pharmacology* (2001), 60(6), 1343-1348.

EXAMPLES

The invention is further illustrated by the following non-limiting examples.

Example 1

7-(1,3-dimethyl-1H-pyrazol-5-yl)-3-(3-{[4-methyl-5-(2-methyl-5-quinolinyl)-4H-1,2,4-triazol-3-yl]thio}propyl)-2,3,4,5-tetrahydro-1H-3-benzazepine Scheme 1

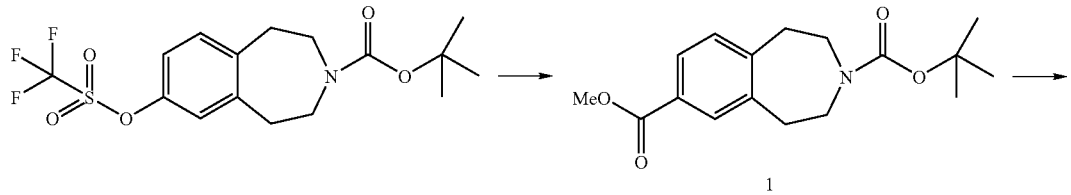

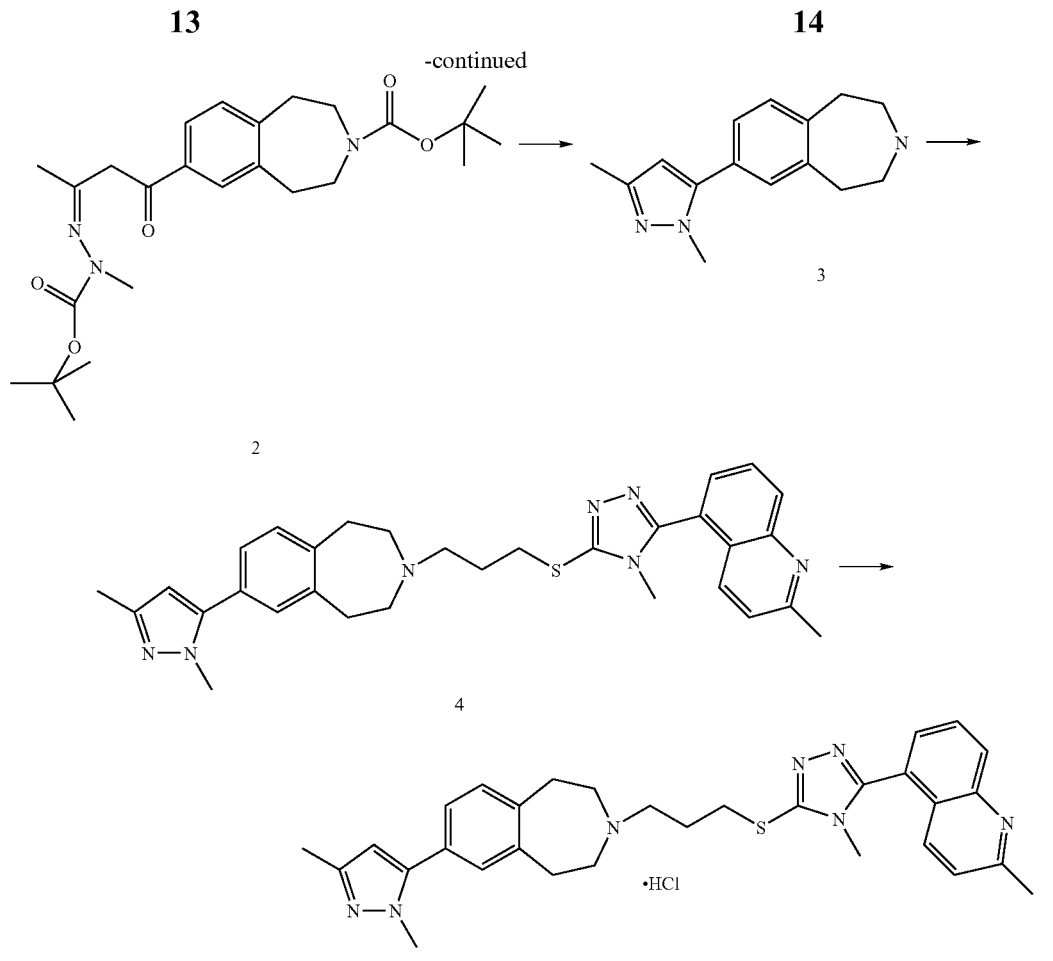

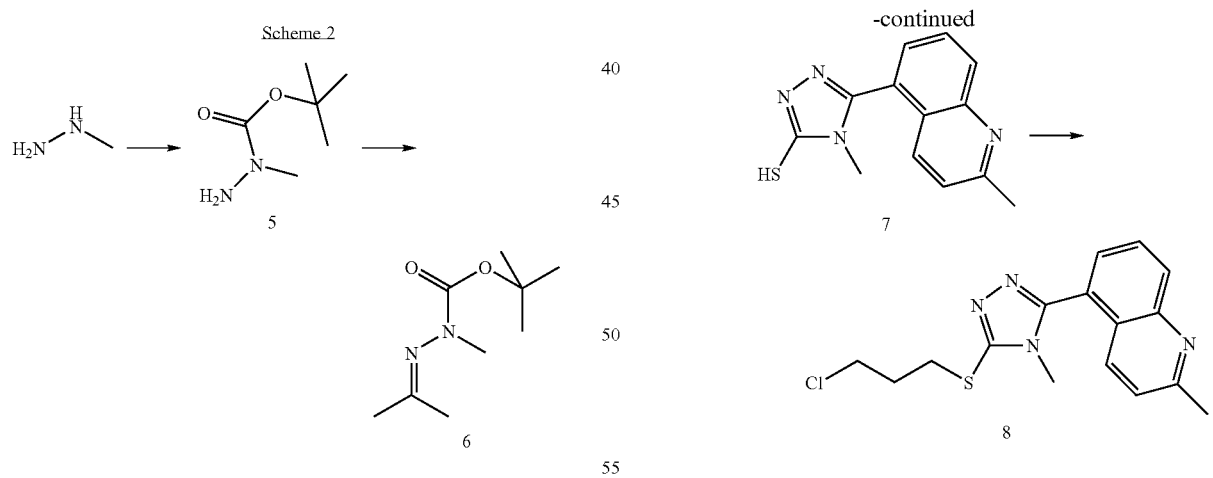

Scheme 1: Route to Example 1

3-(1,1-dimethylethyl)-7-methyl-1,2,4,5-tetrahydro-3H-3-benzazepine-3,7-dicarboxylate (1)

1,1-dimethylethyl-7-{[(trifluoromethyl)sulfonyl]oxy}-1,2,4,5-tetrahydro-3H-3-benzazepine-3-carboxylate (30g) (the synthesis is reported in WO/200240471) palladium (II) acetate (0.51 g) and 1,1'-bis(diphenylphosphino)ferrocene (1.25 g) were dissolved in anhydrous dimethylformamide (75 ml) and methanol (68 ml) under a nitrogen atmosphere, followed by triethylamine (22.74 ml). The solution was purged

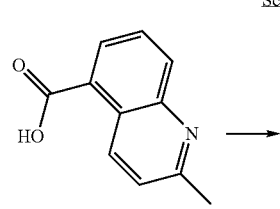

with carbon monoxide for 15 min and stirred under a carbon monoxide balloon at 70° C. for 18 h. The reaction mixture was allowed to reach room temperature, then dichloromethane (300 ml) and water (300 ml) were added. The organic phase was separated, dried with sodium sulphate and evaporated under reduced pressure. The crude product was purified by chromatography on silica gel with 90% cyclohexane-ethyl acetate elution to give the title compound (15g) as an orange oil.

$^1$H-NMR (CDCl$_3$) δ: 7.79 (m, 2H), 7.18 (m, 1H), 3.89 (s, 3H), 3.57 (m, 4H), 2.95 (m, 4H), 1.48 (s, 9H).

1,1-dimethylethyl-7-{(3E)-3-[{[(1,1-dimethylethyl)oxy]carbonyl}(methyl)hydrazono]butanoyl}-1,2,4,5-tetrahydro-3H-3-benzazepine-3-carboxylate (2)

To a stirred solution of 1,1-dimethylethyl 1-methyl-2-(1 methylethylidene)-hydrazinecarboxylate (18.2 g) (intermediate 6) in tetrahydrofuran (80 ml), at 0° C., under a nitrogen atmosphere, lithium bis(trimethylsilyl)amide (115 ml, 1 M/tetrahydrofuran) was added over 0.5h keeping the temperature below 5° C. After stirring for an additional hour, the reaction mixture was added via-cannula to a stirred solution of 3-(1,1-dimethylethyl)-7-methyl-1,2,4,5-tetrahydro-3H-3-benzazepine-3,7-dicarboxylate (10g) (intermediate 1) in anhydrous tetrahydrofuran (70 ml), at 0° C., under a nitrogen atmosphere. Stirring was continued for 2 h after which time water (300 ml) was added and the reaction mixture was extracted with ethyl acetate (800 ml). The organic phase was washed with brine (400 ml), dried with sodium sulphate and concentrated under reduced pressure. The crude product was purified by chromatography on silica gel with 70% cyclohexane-ethyl acetate to give the title compound (12g) as a white solid.

$^1$H-NMR (DMSO) δ: 11.65 (s, 1H), 7.67 (d, 1H), 7.64 (dd, 1H), 7.23 (d, 1H), 5.90 (s, 1H), 3.47 (m, 4H), 3.10 (s, 3H), 2.90 (bm, 4H), 1.98 (s, 3H), 1.41 (s, 18H).

7-(1,3-dimethyl-1H-pyrazol-5-yl)-2,3,4,5-tetrahydro-1H-3-benzazepine (3)

A solution of 1,1-dimethylethyl-7-{(3E)-3-[{[(1,1 dimethylethyl)oxy]carbonyl}(methyl)hydrazono]butanoyl}-1,2,4,5-tetrahydro-3H-3-benzazepine-3-carboxylate (0.5 g) (intermediate 2) in dichloromethane (5 ml) was added dropwise to trifluoroacetic acid (10 ml) under vigorous stirring. After 1 h the reaction mixture was concentrated in vacuo and sodium hydroxide (1N) was added until pH ~12, then the mixture was extracted twice with dichloromethane. The organic phase was dried with sodium sulphate and evaporated to give the title compound (0.26 g).

$^1$H-NMR (DMSO) δ: 7.2-7.1 (m, 3H), 6.06 (s, 1H), 3.73 (s, 3H), 2.9-2.7 (m, 8H), 2.5 (3H).

7-(1,3-dimethyl-1H-pyrazol-5-yl)-3-(3-{[4-methyl-5-(2-methyl-5-quinolinyl)-4H-1,2,4-triazol-3-yl]thio}propyl)-2,3,4,5-tetrahydro-1H-3-benzazepine (4)

To a stirred solution of 7-(1,3-dimethyl-1H-pyrazol-5-yl)-2,3,4,5-tetrahydro-1H-3-benzazepine (4 g) (intermediate 3) in dimethylformamide, at room temperature, 5-{5-[(3-chloropropyl)thio]-4-methyl-4H-1,2,4-triazol-3-yl}-2-methylquinoline (intermediate 8) (6.8 g), sodium iodide (3.06 g) and anhydrous potassium carbonate (2.82 g) were subsequently added and the reaction mixture was warmed to 60° C. and kept reacting for 24 h. After allowing the reaction mixture to reach room temperature, water (70 ml) was added and the reaction mixture was extracted twice with ethyl acetate (50 ml×2). The organic phase was dried with sodium sulphate and after evaporation the crude product was purified by chromatography on silica gel with 100-95% dichloromethane-methanol elution to give the title compound (3.3 g) as a pale yellow solid.

$^1$H-NMR (CDCl$_3$) δ: 8.16 (d, 1H), 8.10 (d, 1H), 7.75 (dd, 1H), 7.54 (d, 1H), 7.3 (d, 1H), 7.12 (m, 3H), 6.03 (m, 1H), 3.78 (s, 3H), 3.43 (t, 2H), 3.38 (s, 3H), 2.95 (bm, 4H), 2.74 (s, 3H), 2.68 (m, 6H), 2.26 (s, 3H), 2.08 (m, 2H).

7-(1,3-dimethyl-1H-pyrazol-5-yl)-3-(3-{([4-methyl-5-(2-methyl-5-quinolinyl)-4H-1,2,4-triazol-3-yl]thio}propyl)-2,3,4,5-tetrahydro-1H-3-benzazepine hydrochloride (Example 1)

To a stirred solution of 7-(1,3-dimethyl-1H-pyrazol-5-yl)-3-(3-{[4-methyl-5-(2-methyl-5-quinolinyl)-4H-1,2,4-triazol-3-yl]thio}propyl)-2,3,4,5-tetrahydro-1H-3-benzazepine (0.5 g) (intermediate 4) in dichloromethane (5 ml), at room temperature, hydrochloridric acid was added dropwise (1.18 ml, 1M/ether). Following solvent evaporation gave the title compound (0.67 g) as a pale yellow solid.

$^1$H-NMR (DMSO) δ: 10.6 (bs, 1H), 8.18 (d, 1H), 8.12 (d, 1H), 7.86 (t, 1H), 7.74 (d, 1H), 7.48 (d, 1H), 7.29 (m, 3H), 6.09 (s, 1H), 3.7 (s, 3H), 3.75-3.65 (bm, 2H), 3.40 (s, 3H), 3.4-3.2 (m, 6H), 3.03 (bm, 4H), 2.67 (s, 3H), 2.24 (m, 2H), 2.11 (s, 3H).

Scheme 2: Route to Intermediate 6

1,1-dimethylethyl 1-methylhydrazine carboxylate (5)

To a solution of methylhydrazine (100g) in anhydrous tetrahydrofuran (1.8 L), cooled at 5° C. and stirred with a mechanic equipment, a solution of di-tert-butyl dicarbonate (498g) in anhydrous tetrahydrofuran (600 ml) was added keeping this temperature for 0.5h. Then water (500 ml) was added, followed by ethyl acetate (2 L). The organic phase was washed with water (2 L), brine (1.6 L) and dried with sodium sulphate, to give after evaporation under reduced pressure the title compound (230g) as a white solid.

$^1$H-NMR (CDCl$_3$) δ: 3.84 (broad, 2H), 3.02 (s, 3H), 1.42 (s, 9H)

1,1-dimethylethyl 1-methyl-2-(1 methylethylidene)-hydrazinecarboxylate (6)

To a stirred solution of 1,1-dimethylethyl 1-methylhydrazine carboxylate (179 g) (intermediate 5) in diethyl ether (2 L), at room temperature, acetone (126 ml), glacial acid acetic (7.7 ml) and sodium acetate (1.27 g) were added. After stirring over night, the reaction mixture was quenched with water, the organic phase was dried with sodium sulphate and the solvent evaporated to give the title compound (182.38 g) as a colourless oil.

$^1$H-NMR (CDCl$_3$) δ: 3.01 (s, 3H), 2.01 (s, 3H), 1.83 (s, 3H), 1.42 (s, 9H).

Scheme 3: Route to Intermediate 8

4-methyl-5-(2-methyl-5-quinolinyl)-2,4-dihydro-3H-1,2,4-triazole-3-thione (7)

Hydroxybenzotriazole (7.8 g), 1-(3-dimethylaminopropyl)-3-ethylcarbodiimide hydrochloride (11 g) and triethylamine were successively added to a stirred solution of 2-methyl-5-quinolinecarboxylic acid (10g) and 4-methyl-3- thiosemicarbazide (6.1 g) in dimethylformamide (200 ml), at 0° C. Following the addiction the reaction mixture was allowed to reach room temperature, the stirred continued over night and then the solvent was evaporated under reduced pressure. The residue was treated with an aqueous sodium hydroxide solution (500 ml, 0.5N) and the mixture was stirred at 80° C. for 3 h, after which time the mixture was cooled to room temperature and the pH adjusted to pH 6 using a aqueous hydrochloridric acid solution (2M) and the resulting precipitatye was filtered and dried in vacuo to give the title compound (11 g) as an off-white solid.

$^1$H-NMR (DMSO) δ: 14 (broad, 1H), 8.17 (dd, 1H), 8.15 (dd, 1H), 7.89 (m, 1H), 7.85 (dd, 1H), 7.52 (dd, 1H), 3.32 (s, 3H), 2.70 (s, 3H).

5-{5-[(3-chloropropyl)thio]-4-methyl-4H-1,2,4-triazol-3-yl}-2-methylquinoline (8)

Sodium hydride (2.65 g, 60% in oil) was added portionwise to stirred absolute ethanole at 0° C., under a nitrogen atmosphere. Then 4-methyl-5-(2-methyl-5-quinolinyl)-2,4-dihydro-3H-1,2,4-triazole-3-thione (21.8 g) (intermediate 7) was added portionwise and the reaction mixture was allowed to reach room temperature. Then 1-bromo-3-chloropropane (12.6 ml) was added over 10 min and the reaction mixture was brought to 80° C. and left to react an additional hour after which time the reaction mixture was allowed to reach room temperature and concentrated under reduced pressure. The crude product was purified by chromatography on silica gel with 90% ethyl acetate-acetone to give the title compound (14.18 g) as a white solid.

$^1$H-NMR (CDCl$_3$) δ: 8.16 (dd, 1H), 8.09 (dd, 1H), 7.76 (dt, 1H), 7.54 (dd, 1H), 7.31 (dd, 1H), 3.75 (t, 1H), 3.49 (t, 1H), 3.40 (s, 3H), 2.75 (s, 3H), 2.38 (m, 2H).

Example 2

7-(1,3-Dimethyl-1H-pyrazol-5-yl)-3-(1-methyl-3-{[4-methyl-5-(2-methyl-5-quinolinyl)-4H-1,2,4-triazol-3-yl]thio}propyl)-2,3,4,5-tetrahydro-1H-3-benzazepine hydrochloride

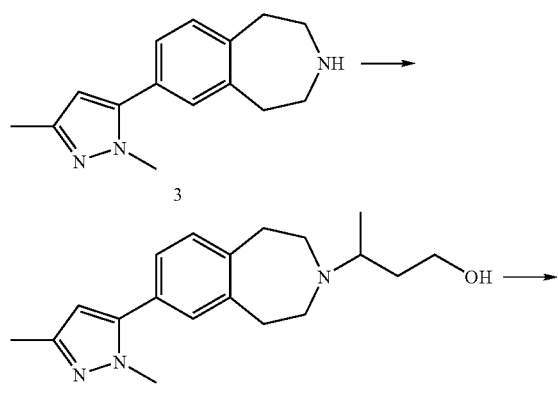

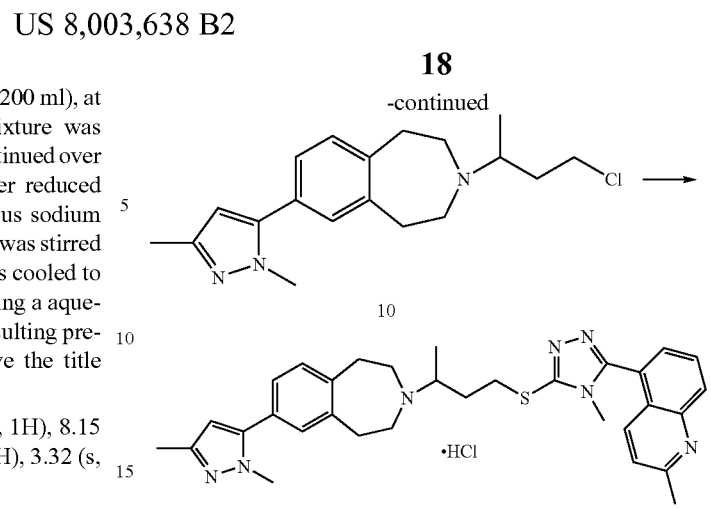

Example 2

3-[7-(1,3-Dimethyl-1H-pyrazol-5-yl)-1,2,4,5-tetrahydro-3H-3-benzazepin-3-yl]-1-butanol (9)

To a stirred solution of 7-(1,3-dimethyl-1H-pyrazol-5-yl)-2,3,4,5-tetrahydro-1H-3-benzazepine (0.5 g) (intermediate 3) in tetrahydrofuran (5 ml), at room temperature, 4-hydroxy-2-butanone (0.22 g), glacial acetic acid (0.12 ml) and sodium triacetoxyborohydride (0.53 g) were subsequently added. After stirring over night the mixture was made alkaline with 1N aqueous sodium hydroxide and extracted with dichloromethane. The organic phase was dried with sodium sulphate and evaporated under reduced pressure. The crude product was purified by chromatography on silica gel with 70% cyclohexane-ethyl acetate to give the title compound (0.25 g) as a white solid.

$^1$H-NMR (CDCl$_3$) δ: 7.30-7.20 (m, 3H), 6.15 (s, 1H), 3.89 (s, 3H), 3.85-3.65 (m, 2H), 3.15-2.90 (m, 5H), 2.82 (m, 2H), 2.68 (m, 2H), 2.38 (s, 3H), 2.09 (m, 1H), 1.81 (m, 1H), 1.03 (d, 3H).

3-(3-Chloro-1-methylpropyl)-7-(1,3-dimethyl-1H-pyrazol-5-yl)-2,3,4,5-tetrahydro-1H-3-benzazepine (10)

To a stirred solution of 3-[7-(1,3-dimethyl-1H-pyrazol-5-yl)-1,2,4,5-tetrahydro-3H-3-benzazepin-3-yl]-1-butanol (0.25 g) (intermediate 9) in chloroform (8 ml), at room temperature, thionyl chloride (0.11 ml) was added dropwise. After 2h, saturated aqueous sodium hydrogencarbonate (5 ml) was added, the reaction mixture was extracted with dichloromethane (15 ml), the organic phase dried with sodium sulphate and the solvent evaporated under reduced pressure. The crude product was purified by chromatography on silica gel with 80% cyclohexane-ethyl acetate to give the title compound (0.23 g) as a white solid.

$^1$H-NMR (CDCl$_3$) δ: 7.15-7.10 (m, 3H), 6.04 (s, 1H), 3.94 (m, 1H), 3.82 (m, 1H), 3.04 (m, 1H), 3.05-2.85 (m, 6H), 2.61 (m, 2H), 2.39 (s, 3H), 2.00 (m, 1H), 1.32 (m, 1H), 0.93 (d, 3H).

7-(1,3-Dimethyl-1H-pyrazol-5-yl)-3-(1-methyl-3-{[4-methyl-5-(2-methyl-5-quinolinyl)-4H-1,2,4-triazol-3-yl]thio}propyl)-2,3,4,5-tetrahydro-1H-3-benzazepine hydrochloride To a stirred solution of 3-(3-chloro-1-methylpropyl)-7-(1,3-dimethyl-1H-pyrazol-5-yl)-2,3,4,5-tetrahydro-1H-3-benzazepine (0.10 g) (intermediate 10) and 4-methyl-5-(2-methyl-5-quinolinyl)-2,4-dihydro-3H-1,2,4-triazole-3-thione (0.093 g) (intermediate 7) in dimethylformamide (2 ml), at room temperature, sodium iodide (0.040 g) and anhydrous potassium carbonate were subsequently added. Then the reaction mixture was warmed to 70° C. and stirring continued for 3 h after which time the mixture was allowed to reach room temperature and the solvent evaporated under reduced pressure. The residue was treated with water (10 ml), extracted with ethyl acetate (20 ml). The organic phase was dried with sodium sulphate and after evaporation the crude product was purified by chromatography on silica gel with 100-95% dichloromethane-methanol elution to give 7-(1,3-dimethyl-1H-pyrazol-5-yl)-3-(1-methyl-3-{[4-methyl-5-(2-methyl-5-quinolinyl)-4H-1,2,4-triazol-3-yl]thio}propyl)-2,3,4,5-tetrahydro-1H-3-benzazepine (0.040 g) as a pale yellow solid. This product was dissolved in dichloromethane (2 ml), and hydrochloridric acid was added dropwise (0.072 ml, 1M/ether), at room temperature. Following solvent evaporation gave the title compound (0.042 g) as a yellow solid.

$^1$H-NMR (DMSO-d$_6$) δ: 10.58 (bs, 1H), 8.50 (bs, 1H), 8.27 (d, 1H), 8.00 (t, 1H), 7.89 (d, 1H), 7.67 (d, 1H), 7.28 (m, 3H), 6.09 (s, 2H), 3.7 (s, 3H), 3.60 (bm, 2H), 3.60-3.50 (m, 2H), 3.55 (m, 1H), 3.41 (s, 3H), 3.40 (m, 1H), 3.22 (m, 1H), 3.15-2.95 (m, 4H), 2.79 (s, 3H), 2.45 (m, 1H), 2.11 (s, 3H), 2.00 (m, 1H), 1.32 (d, 3H)

Preparation 11: 3-[(3-Chloropropyl)thio]-4-methyl-5-(4-methyl-1,3-oxazol-5-yl)-4H-1,2,4-triazole

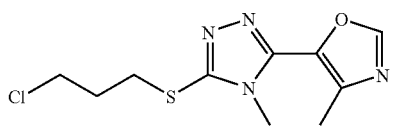

Ethyl-2-chloroacetoacetate (1 wt; 1 eq., 1000 g) was aged with formamide (0.68 vol; ca. 2.8 eq.) and the resulting solution was heated to 120° C. After 5 hours the mixture was allowed to cool to room temperature and allowed to age under nitrogen over night. The mixture was treated with NaOH (3 M, 6 vol, reaction moderately exothermic) and stirred at room temperature for 4 hours. Ethyl acetate (6 vol) was added and the phases allowed to separate. The organic layer was discarded while the aqueous was acidified with conc. (32%) aqueous HCl to pH 2 (ca. 2.0 vol). A precipitate started to form. The suspension was treated with AcOEt (8 vol) and vigorously stirred until the bulk of the precipitate had dissolved. The aqueous phase was further extracted with AcOEt twice (6 vol each) and the combined organic layers distilled to low volume (again a suspension was observed at low volume). Fresh AcOEt (8 vol) was added and the mixture evaporated to dryness. The collected solid was placed in the oven at 40° C. over night under reduced pressure to give 4-methyl-1,3-oxazole-5-carboxylic acid (498 g, 64.5%). This material (498 g, 1 wt) was dissolved in dry tetrahydrofuran (5 vol), under nitrogen, cooled to 0° C. DCC (1.62 wt, 1 eq) was added portionwise followed by HOBt (1.07 wt, 1 eq). The mixture was warmed to 25±2° C. and stirred for 30 min. 4-Methyl-3-thiosemicarbazide (0.83 wt, 1 eq) was then added and the mixture further stirred for 2 h at 25±2° C. The mixture was filtered and the cake was washed with fresh tetrahydrofuran (1 vol) and dried on the filter for a few hours. The cake was suspended in 1 M aqueous NaOH (13 vol) and heated to 70° C. for 30 min. After this time, the mixture was cooled to 25±2° C. and a solid was removed by filtration. The cake was washed with 1 M aqueous NaOH (10 vol). The combined mother liquors were cooled to 0° C. and acidified to ca. pH 5 with HCl (aqueous, 16%; NOTE: keep temperature while adding HCl below +10° C.). The suspended product was isolated by filtration washing with water (2×3 vol). The cake was dried at 40° C. for 18 h in high vacuum to obtain 4-methyl-5-(4-methyl-1,3-oxazol-5-yl)-2,4-dihydro-3H-1,2,4-triazole-3-thione (respectively a tautomeric form thereof; 290 g, 37%). NaOEt (21% solution in EtOH, 2.08 vol, 1.1 eq) was added to EtOH (20 vol) under nitrogen atmosphere. 4-Methyl-5-(4-methyl-1,3-oxazol-5-yl)-2,4-dihydro-3H-1,2,4-triazole-3-thione (respectively a tautomeric form thereof; 290 g, 1 wt) was added in one portion and the resulting mixture stirred at 25±2° C. until a clear solution was obtained. Then 1-bromo-3-chloropropane (0.54 vol, 1.1 eq) was added and the solution stirred at 40° C. for 24 h then cooled to 25° C. After filtration water (20 vol) was added and the ethanolic phase was removed by vacuum distillation (internal temperature ~40° C.). The mixture was extracted with EtOAc (41 vol). The aqueous layer was removed and the organic phase was evaporated to dryness. Dichloromethane (4 vol) was added. The organic solution is purified through a short silica gel column (18 wt of silica), eluting with EtOAc (200 vol) to give the title compound as a solid foam (267.64 g, 66%).

NMR ($^1$H, CDCl$_3$): δ 7.90 (s, 1H), 3.70 (s, 5H), 3.40 (t, 2H), 2.52 (s, 3H), 2.30 (m, 2H). MS (m/z): 273 [MH]$^+$.

Preparation 12: 5-{5-[(3-chloropropyl)thio]-4-methyl-4H-1,2,4-triazol-3-yl}-8-fluoro-2-methylquinoline

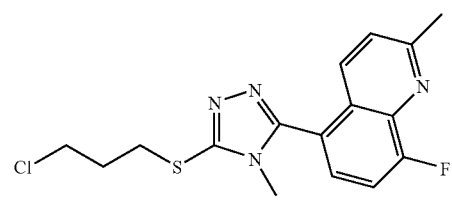

The title compound was prepared as reported in WO 2002040471

MS (m/z): 351 [MH]$^+$

Preparation 13: 3-[(3-chloropropyl)thio]-4-methyl-5-[4-(trifluoromethyl)phenyl]-4H-1,2,4-triazole

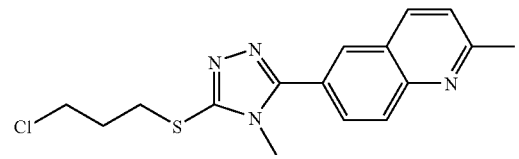

The title compound was prepared as reported in WO 2002040471

MS (m/z): 333 [MH]$^+$

Preparation 14: 3-[(3-chloropropyl)thio]-5-(3,4-difluorophenyl)-4-methyl-4H-1,2,4-triazole

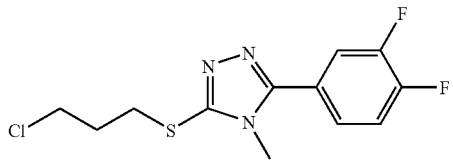

The title compound was prepared as reported in WO 2002040471

MS (m/z): 304 [MH]$^+$

Preparation 15: 3-[(3-chloropropyl)thio]-4-methyl-5-[4-(trifluoromethyl)phenyl]-4H-1,2,4-triazole

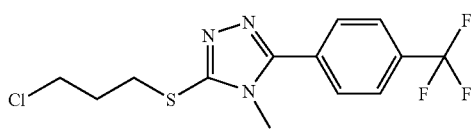

The title compound was prepared as reported in WO 2002040471

MS (m/z): 336 [MH]$^+$

Preparation 16: 3-(3-chloropropyl)-7-(1,3-dimethyl-1H-pyrazol-5-yl)-2,3,4,5-tetrahydro-1H-3-benzazepine

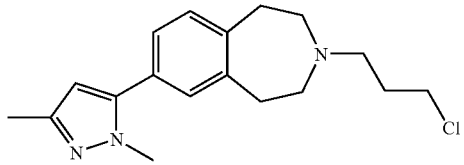

To a solution of 7-(1,3-dimethyl-1H-pyrazol-5-yl)-2,3,4,5-tetrahydro-1H-3-benzazepine (0.5 g) in dry THF (10 ml), diisopropylethylamine (0.85 ml) and 1-bromo-3-chloropropane (0.47 mL) were added and the resulting mixture was refluxed for 7 hours. After cooling at room temperature it was diluted with ethyl acetate (30 ml) washed twice with a saturated solution of NaHCO$_3$ in water (20 ml), dried over Na$_2$SO$_4$ and concentrated under reduced pressure. The crude was purified by biotage chromatography using a silica 25 M+ cartridge and eluting with cHex/EtOAc 8:2 to give the title compound as a colourless oil (0.57 g).

NMR ($^1$H, CDCl$_3$): δ=7.1 (m, 3H) 6.05 (s, 3H), 3.81 (s, 3H), 3.64 (t, 2H), 2.93 (m, 4H), 2.66 (m, 6H), 2.28 (s, 2H), 1.97 (m, 2H). MS (m/z): 318 [MH]$^+$

Preparation 17: 7-(4-chloro-1,3-dimethyl-1H-pyrazol-5-yl)-2,3,4,5-tetrahydro-1H-3-benzazepine

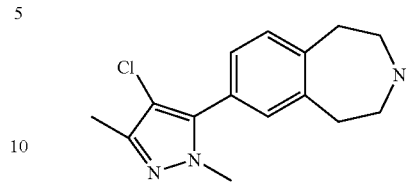

To a stirred solution of 7-(1,3-dimethyl-1H-pyrazol-5-yl)-2,3,4,5-tetrahydro-1H-3-benzazepine (0.37 g) and triethylamine (0.3 mL) in DCM (5 mL), at 0° C., trifluoroacetic anhydride (0.26 mL) was added dropwise. The ice bath was removed and the stirring continued for 4 h after which time aqueous saturated NaHCO$_3$ (10 mL) was added, the reaction mixture was extracted twice with diethyl ether (10 mL), the organic phase dried over Na$_2$SO$_4$ and evaporated under reduced pressure to give the correspondent N-trifluoacetyl benzazepine derivative in 0.5 g yield. This product (0.11g) was dissolved in DMF (1 mL) and N-chlorosuccinimide (47 mg) was added, the reaction was warmed to 50° C. and stirred for 1 h. Then the reaction mixture was allowed to reach RT, water was added (4 mL), the mixture was extracted twice with ethyl ether (5 mL), the organic phase dried over Na$_2$SO$_4$ and evaporated under reduced pressure. The crude product so obtained was dissolved in MeOH (10 mL) and a solution of K$_2$CO$_3$ (0.36 g) in water (10 mL) was added, then the mixture was warmed to 55° C. and stirred for 2 h. The reaction mixture was concentrated under reduced pressure, extracted twice with DCM (10 mL), the organic phase dried over Na$_2$SO$_4$ and the solvent evaporated under reduced pressure to give the title compound (0.17 g) that was used as such.

MS (m/z): 276.1 [MH]$^+$

Preparation 18: 5-(8-fluoro-2-methyl-5-quinolinyl)-4-methyl-2,4-dihydro-3H-1,2,4-triazole-3-thione

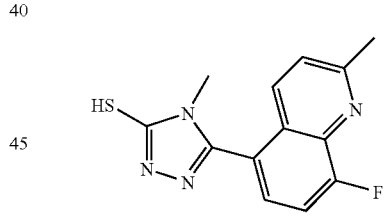

The title compound was prepared as reported in WO 2002040471

MS (m/z): 275.1 [MH]$^+$

Preparation 19: 4-methyl-5-(2-methyl-6-quinolinyl)-2,4-dihydro-3H-1,2,4-triazole-3-thione

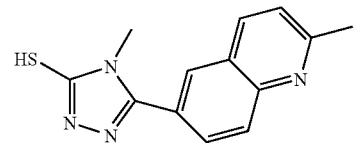

The title compound was prepared as reported in WO 2002040471

MS (m/z): 257 [MH]$^+$

Example 3

7-(1,3-dimethyl-1H-pyrazol-5-yl)-3-[3-({4-methyl-5-[4-(trifluoromethyl)phenyl]-4H-1,2,4-triazol-3-yl}thio)propyl]-2,3,4,5-tetrahydro-1H-3-benzazepine hydrochloride

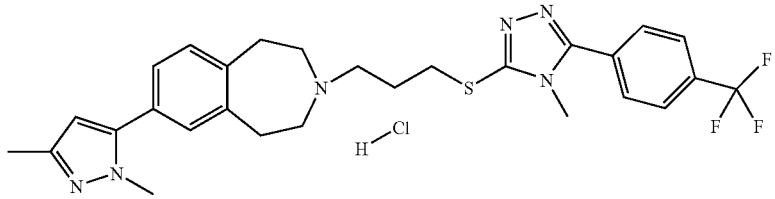

To a stirred solution of 7-(1,3-dimethyl-1H-pyrazol-5-yl)-2,3,4,5-tetrahydro-1H-3-benzazepine (80 mg) in dimethylformamide (0.6 mL) at room temperature, 3-[(3-chloropropyl)thio]-4-methyl-5-[4-(trifluoromethyl)phenyl]-4H-1,2,4-triazole (133 mg), sodium iodide (60 mg) and anhydrous potassium carbonate (55 mg) were subsequently added and the reaction mixture was warmed to 60° C. and kept reacting for 24 h. After allowing the reaction mixture to reach room temperature, water (2 ml) was added and the reaction mixture was extracted twice with ethyl acetate (4 mL). The organic phase was dried over sodium sulphate and after evaporation the crude product was purified by chromatography on silica gel with 100-95% dichloromethane-methanol elution to give 99 mg of the free base of the title compound. To a solution of this material in dichloromethane (1 mL), at room temperature, HCl (1M in Et$_2$O, 0.18 mL) was added, the solvent evaporated under reduced pressure and the material thus obtained triturated with Et$_2$O to give 103 mg of the title compound as a white solid.

NMR ($^1$H, DMSO): δ 10.48 (bs, 1H), 8.00 (m, 4H), 7.30 (m, 3H), 6.2 (s, 1H), 3.76-3.68 (2s, 6H), 3.70 (bm, 2H), 3.50-3.20, 3.10 (bm, 10H), 2.24 (quint., 2H), 2.17 (s, 3H). MS (m/z): 541.0 [MH]$^+$.

Example 4

3-(3-{[5-(3,4-difluorophenyl)-4-methyl-4H-1,2,4-triazol-3-yl]thio}propyl)-7-(1,3-dimethyl-1H-pyrazol-5-yl)-2,3,4,5-tetrahydro-1H-3-benzazepine hydrochloride

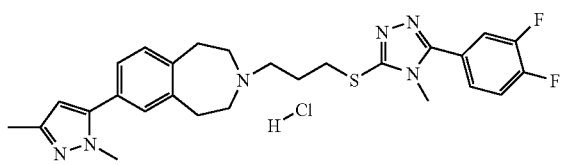

The title compound was prepared in analogy to the method described in Example 3 in 99 mg yield as a white solid from 3-[(3-chloropropyl)thio]-5-(3,4-difluorophenyl)-4-methyl-4H-1,2,4-triazole (121 mg).

NMR ($^1$H, DMSO): δ 10.60 (bs, 1H), 7.85 (dt, 1H), 7.70-7.76 (m, 2H), 7.35 (m, 3H), 6.15 (s, 1H), 3.76 (s, 3H), 3.71 (bm, 2H), 3.65 (s, 3H), 3.40-3.20 (m, 6H), 3.09 (bm, 4H), 2.23 (m, 2H), 2.17 (s, 3H). MS (m/z): 509.0 [MH]$^+$.

Example 5

7-(1,3-dimethyl-1H-pyrazol-5-yl)-3-(3-{[4-methyl-5-(4-methyl-1,3-oxazol-5-yl)-4H-1,2,4-triazol-3-yl]thio}propyl)-2,3,4,5-tetrahydro-1H-3-benzazepine hydrochloride The title compound was prepared in analogy to the method described in Example 3 in 100 mg yield as a white solid from: 3-[(3-chloropropyl)thio]-4-methyl-5-(4-methyl-1,3-oxazol-5-yl)-4H-1,2,4-triazole (100 mg).

NMR ($^1$H, DMSO): δ 10.25 (bs, 1H), 8.59 (s, 1H), 7.35 (m, 3H), 6.15 (s, 1H), 3.76 (s, 3H), 3.71 (s, 3H), 3.80-3.70 (bm, 2H), 3.40-3.20 (m, 6H), 3.09 (bm, 4H), 2.40 (s, 3H), 2.21 (m, 2H), 2.17 (s, 3H). MS (m/z): 509.0 [MH]$^+$.

Example 6

7-(4-chloro-1,3-dimethyl-1H-pyrazol-5-yl)-3-(3-{[4-methyl-5-(4-methyl-1,3-oxazol-5-yl)-4H-1,2,4-triazol-3-yl]thio}propyl)-2,3,4,5-tetrahydro-1H-3-benzazepine hydrochloride The title compound was prepared in analogy to the method described in Example 3 in 24 mg yield as a white solid from 7-(4-chloro-1,3-dimethyl-1H-pyrazol-5-yl)-2,3,4,5-tetrahydro-1H-3-benzazepine (55 mg) and 3-[(3-chloropropyl)thio]-5-(3,4-difluorophenyl)-4-methyl-4H-1,2,4-triazole (65 mg).

NMR ($^1$H, DMSO): δ 10.16 (bs, 1H), 8.57 (s, 1H), 7.36 (m, 3H), 3.68 (s, 6H), 3.80-3.70 (bm, 2H), 3.26-3.11 (m, 10H), 2.37 (s, 3H), 2.19 (m, 2H), 2.16 (s, 3H). MS (m/z): 512.0 [MH]$^+$.

Example 7

7-(1,3-dimethyl-1H-pyrazol-5-yl)-3-(3-{[5-(8-fluoro-2-methyl-5-quinolinyl)-4-methyl-4H-1,2,4-triazol-3-yl]thio}propyl)-2,3,4,5-tetrahydro-1H-3-benzazepine hydrochloride

Example 8

7-(1,3-dimethyl-1H-pyrazol-5-yl)-3-(3-{[4-methyl-5-(2-methyl-6-quinolinyl)-4H-1,2,4-triazol-3-yl]thio}propyl)-2,3,4,5-tetrahydro-1H-3-benzazepine hydrochloride To a solution of the 3-thio-5-aryl-1,2,4-triazoles (0.126 mmol) in dry acetonitrile (2 ml) 2-tert-butylimino-2-diethylamino-1,3-dimethyl-perhydro-1,3,2-diaza-phosphorine on polystyrene (85 mg, 2.2 mmol/g) was added and the resulting mixture was shaken for 1 hour at room temperature then 3-(3-chloropropyl)-7-(1,3-dimethyl-1H-pyrazol-5-yl)-2,3,4,5-tetrahydro-1H-3-benzazepine (40 mg) was added and the resulting mixture was shaken at 70° C. for three hours. After cooling the resin was filtered off, washed with methanol (2 ml) and then the solvent was removed under reduced pressure. Purifications were carried out using mass directed HPLC using a Waters XTerra Prep MS C18 10 μm, 30×150 mm column using the following conditions

|  | Time | Flow | % A | % B |
|---|---|---|---|---|
| Prerun | 0 | 40 ml/min | 99 | 1 |
|  | 1 | 40 ml/min | 99 | 1 |
| Run | 0 | 40 ml/min | 99 | 1 |
|  | 10 | 40 ml/min | 75 | 25 |
|  | 14.5 | 40 ml/min | 10 | 90 |
|  | 15 | 40 ml/min | 0 | 100 |
| Postrun | 0 | 40 ml/min | 0 | 100 |
|  | 0.2 | 45 ml/min | 0 | 100 |
|  | 1.5 | 45 ml/min | 0 | 100 |
|  | 2 | 40 ml/min | 0 | 100 |

A = H20 + 0.1% formic acid, B = ACN + 0.1% formic acid

Then solvent was removed under reduced pressure to give title compounds as formate salts. The residues were taken up with methanol (1 ml) and loaded on SCX SPE cartridges (1g), washed with methanol (3 ml) and eluted with a 2N ammonia solution in methanol (3 ml) then solvent was removed under reduced pressure. The residues were taken up with dichloromethane (1 ml) and a 1.0 N HCl solution in diethylether was added (0.126 mmol) then solvent was removed under reduced pressure to give title compounds as hydrochloride salts.

HPLC: Analytical
  Column: X Terra MS C18 5 mm, 50×4.6 mm
  Mobile phase: A: NH4HCO3 sol. 10 mM, pH10; B: CH3CN
  Gradient: 10% (B) for 1 min, from 10% (B) to 95% (B) in 12 min, 95% (B) for 3 min
  Flow rate: 1 ml/min
  UV wavelength range: 210-350 nm Mass range: 100-900 amu Ionization: ES+

| Example and Name | Chemical structure | Retention time (min) | Analytical data |
|---|---|---|---|
| Example 7<br>7-(1,3-dimethyl-1H-pyrazol-5-yl)-3-(3-{[5-(8-fluoro-2-methyl-5-quinolinyl)-4-methyl 4H-1,2,4-triazol-3-yl]thio}propyl)-2,3,4,5-tetrahydro-1H-3-benzazepine hydrochloride | (structure) | 8.21 | MS (m/z): 556 [MH]$^+$ |
| Example 8<br>7-(1,3-dimethyl-1H-pyrazol-5-yl)-3-(3-{[4-methyl-5-(2-methyl-6-quinolinyl)-4H-1,2,4-triazol-3-yl]thio}propyl)-2,3,4,5-tetrahydro-1H-3-benzazepine hydrochloride | (structure) | 8.29 | NMR (1H, CD3OD):<br>d 9.20 (d, 1H), 8.77 (d, 1H), 8.52 (dd, 1H), 8.40 (d, 1H), 7.51 (m, 3H), 6.57 (s, 1H), 3.98 (s, 3H), 3.9 (bm, 2H), 3.89 (s, 3H), 3.5 (m, 4H), 3.6-3.2 (m, 6H), 3.10 (s, 3H), 2.46 (s, 3H), 2.42 (m, 2H) |

The invention claimed is:

1. A compound of formula (I) or a salt thereof:

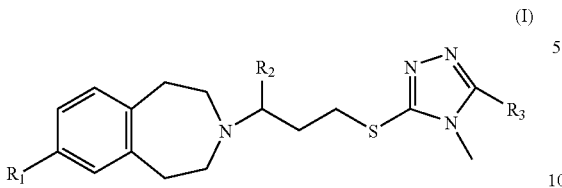
(I)

wherein:

$R_1$ is pyrazolyl substituted by two or three substituents independently selected from halogen, $C_{1-4}$alkyl and halo$C_{1-4}$alkyl;

$R_2$ is hydrogen or methyl; and $R_3$ is quinolinyl, oxazolyl or phenyl, each of which is optionally substituted by one or two halogen, $C_{1-4}$alkyl or halo$C_{1-4}$alkyl.

2. A compound as claimed in claim 1, wherein $R_1$ is pyrazol-5-yl or pyrazol-3-yl.

3. A compound as claimed in claim 2, wherein $R_1$ is:

(a) a group of formula (i):

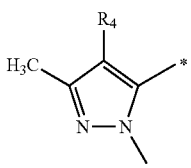
(i)

wherein $R_4$ is hydrogen or halogen and $R_5$ is $C_{1-4}$alkyl or halo$C_{1-4}$alkyl;

or (b) a group of formula (ii):

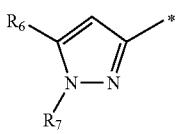
(ii)

wherein $R_6$ and $R_7$ are independently $C_{1-6}$alkyl.

4. A compound as claimed in claim 1, wherein $R_3$ is quinolinyl substituted by one or two $C_{1-4}$alkyl.

5. A compound as claimed in claim 1 which is:

7-(1,3-dimethyl-1H-pyrazol-5-yl)-3-(3-{[4-methyl-5-(2-methyl-5-quinolinyl)-4H-1,2,4-triazol-3-yl]thiolpropyl)-2,3,4,5-tetrahydro-1H-3-benzazepine;

7-(1,3-Dimethyl-1H-pyrazol-5-yl)-3-(1-methyl-3-{[4-methyl-5-(2-methyl-5-quinolinyl)-4H-1,2,4-triazol-3-yl]thio}propyl)-2,3,4,5-tetrahydro-1H-3-benzazepine;

7-(1,3-dimethyl-1H-pyrazol-5-yl)-3-[3-({4-methyl-5-[4-(trifluoromethyl)phenyl]-4H-1,2,4-triazol-3-yl}thio)propyl]-2,3,4,5-tetrahydro-1H-3-benzazepine;

3-(3{[5-(3,4-difluorophenyl)-4-methyl-4H-1,2,4-triazol-3-yl]thio}propyl)-7-(1,3-dimethyl-1H-pyrazol-5-yl)-2,3,4,5-tetrahydro-1H-3-benzazepine;

7-(1,3-dimethyl-1H-pyrazol-5-yl)-3-(3-{[4-methyl-5-(4-methyl-1,3-oxazol-5-yl)-4H-1,2,4-triazol-3-yl]thio}propyl)-2,3,4,5-tetrahydro-1H-3-benzazepine;

7-(4-chloro-1,3-dimethyl-1H-pyrazol-5-yl)-3-(3-{[4-methyl-5-(4-methyl-1,3-oxazol-5-yl)-4H-1,2,4-triazol-3-yl]thio}propyl)-2,3,4,5-tetrahydro-1H-3-benzazepine;

7-(1,3-dimethyl-1H-pyrazol-5-yl)-3-(3-{[5-(8-fluoro-2-methyl-5-quinolinyl)-4-methyl-4H-1,2,4-triazol-3-yl]thio}propyl)-2,3,4,5-tetrahydro-1H-3-benzazepine;

7-(1,3-dimethyl-1H-pyrazol-5-yl)-3-(3-{[4-methyl-5-(2-methyl-6-quinolinyl)-4H-1,2,4-triazol-3-yl]thio}propyl)-2,3,4,5-tetrahydro-1H-3-benzazepine;

or a salt thereof.

6. A pharmaceutical composition comprising a compound as claimed in claim 1 and a pharmaceutically acceptable carrier.

* * * * *